(12) United States Patent
Matthis et al.

(10) Patent No.: US 8,845,702 B2
(45) Date of Patent: Sep. 30, 2014

(54) BONE ANCHORING ELEMENT

(75) Inventors: Wilfried Matthis, Weisweil (DE); Lutz Biedermann, VS-Villingen (DE)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 0 days.

(21) Appl. No.: 13/617,923

(22) Filed: Sep. 14, 2012

(65) Prior Publication Data

US 2013/0072993 A1 Mar. 21, 2013

Related U.S. Application Data

(63) Continuation of application No. 11/482,374, filed on Jul. 7, 2006, now Pat. No. 8,292,932.

(60) Provisional application No. 60/697,669, filed on Jul. 8, 2005.

(30) Foreign Application Priority Data

Jul. 8, 2005 (EP) .................................... 05014839

(51) Int. Cl.
*A61B 17/04* (2006.01)
*A61B 17/86* (2006.01)
*A61F 2/08* (2006.01)
*A61B 17/00* (2006.01)

(52) U.S. Cl.
CPC .......... *A61B 17/8625* (2013.01); *A61B 17/864* (2013.01); *A61B 17/8685* (2013.01); *A61B 17/866* (2013.01); *A61B 2017/00867* (2013.01); *A61B 2017/8655* (2013.01)
USPC .......................................... 606/313; 606/310

(58) Field of Classification Search
USPC ........................................ 606/310, 313, 323
See application file for complete search history.

(56) References Cited

U.S. PATENT DOCUMENTS

| | | | |
|---|---|---|---|
| 3,987,698 A | 10/1976 | Rabe | |
| 4,122,431 A | 10/1978 | Peraldi | |
| 4,331,423 A | 5/1982 | Yanney, Jr. | |
| 4,625,725 A | 12/1986 | Davison et al. | |
| 4,976,715 A | 12/1990 | Bays et al. | |
| 5,209,753 A | 5/1993 | Biedermann et al. | |
| 5,380,334 A | 1/1995 | Torrie et al. | |

(Continued)

FOREIGN PATENT DOCUMENTS

| | | |
|---|---|---|
| CH | 682 450 A5 | 9/1993 |
| DE | 19801219 A1 | 7/1999 |

(Continued)

OTHER PUBLICATIONS

OA dated Mar. 27, 2009 for U.S. Appl. No. 11/063,049 (11 sheets).

(Continued)

*Primary Examiner* — Sameh Boles
(74) *Attorney, Agent, or Firm* — Christie, Parker & Hale, LLP

(57) ABSTRACT

A bone anchoring element includes a shaft for anchoring in a bone, the shaft having a tubular body. The shaft comprises a plurality of barb elements, wherein each barb element is formed as continuous one-piece part with the tubular body. Each barb element is moveable between a first position adjacent to the tubular body and a second position further from the tubular body than the first position. The barb elements are arranged along at least one helical line around an axis of the shaft.

15 Claims, 4 Drawing Sheets

(56) References Cited

U.S. PATENT DOCUMENTS

| | | | |
|---|---|---|---|
| 5,562,704 | A | 10/1996 | Tamminmäki et al. |
| 5,577,912 | A | 11/1996 | Prins |
| 5,601,558 | A | 2/1997 | Torrie et al. |
| 5,645,589 | A | 7/1997 | Li |
| 5,662,654 | A | 9/1997 | Thompson |
| 5,690,649 | A | 11/1997 | Li |
| 5,735,898 | A | 4/1998 | Brånemark |
| 5,814,071 | A | 9/1998 | McDevitt et al. |
| 5,849,004 | A | 12/1998 | Bramlet |
| 5,858,020 | A | 1/1999 | Johnson et al. |
| 6,086,303 | A | 7/2000 | Flückiger |
| 6,187,009 | B1 | 2/2001 | Herzog et al. |
| 6,302,885 | B1 | 10/2001 | Essiger |
| 6,375,458 | B1 | 4/2002 | Moorleghem et al. |
| 6,428,317 | B1 | 8/2002 | Abel |
| 6,447,513 | B1 | 9/2002 | Griggs |
| 6,660,008 | B1 | 12/2003 | Foerster et al. |
| 6,843,791 | B2 | 1/2005 | Serhan |
| 7,879,036 | B2 | 2/2011 | Biedermann et al. |
| 8,080,044 | B2 | 12/2011 | Biedermann et al. |
| 8,292,232 | B1 | 10/2012 | Andrews et al. |
| 8,486,121 | B2 | 7/2013 | Biedermann et al. |
| 2003/0045885 | A1 | 3/2003 | Margulies et al. |
| 2004/0122431 | A1 | 6/2004 | Biedermann et al. |
| 2004/0267264 | A1 | 12/2004 | Konieczynski et al. |
| 2005/0055026 | A1 | 3/2005 | Biedermann et al. |
| 2005/0159749 | A1 | 7/2005 | Levy et al. |
| 2005/0165395 | A1 | 7/2005 | Orbay et al. |
| 2005/0187555 | A1 | 8/2005 | Biedermann et al. |
| 2005/0203522 | A1 | 9/2005 | Vaughn |
| 2006/0264952 | A1 | 11/2006 | Nelson et al. |

FOREIGN PATENT DOCUMENTS

| | | |
|---|---|---|
| DE | 10 2004 009 429 A1 | 9/2005 |
| EP | 0714643 A1 | 6/1996 |
| JP | 06-292686 A | 10/1994 |
| JP | 10-509612 A | 9/1998 |
| KR | 10-2005-0058992 | 6/2005 |
| WO | WO 96/14798 | 5/1996 |

OTHER PUBLICATIONS

OA dated Dec. 8, 2009 for U.S. Appl. No. 11/063,049 (11 sheets).
OA dated Nov. 8, 2008 for U.S. Appl. No. 11,499,034 (8 sheets).
OA dated May 28, 2009 for U.S. Appl. No. 11,499,034 (12 sheets).
OA dated Oct. 26, 2009 for U.S. Appl. No. 11,499,034 (9 sheets).
OA dated Mar. 29, 2010 for U.S. Appl. No. 11,499,034 (13 sheets).
OA dated Dec. 26, 2008 for U.S. Appl. No. 11,646,973 (9 sheets).
OA dated Jun. 25, 2009 for U.S. Appl. No. 11,646,973 (10sheets).
OA dated Oct. 28, 2009 for U.S. Appl. No. 11,646,973 (8 sheets).
OA dated Jan. 22, 2010 for U.S. Appl. No. 11,646,973 (9 sheets).
OA dated May 11, 2010 for U.S. Appl. No. 11,646,973 (7 sheets).
OA dated Oct. 13, 2010 for U.S. Appl. No. 11,646,973 (9 sheets).
European Search Report dated Aug. 25, 2005 for EPO Application No. 05014839.4, European Search Report mailed Sep. 22, 2005; Biedermann Motech GmbH (6 pages).
European Search Report for European Application No. 05014839.4-2318 dated Sep. 22, 2005, 6 pages.
OA dated Oct. 3, 2013 for U.S. Appl. No. 11/063,049, 14 pages.
OA dated Dec. 14, 2012 for U.S. Appl. No. 12/908,826, 7 pages.
OA dated Jul. 30, 2012 for U.S. Appl. No. 13/285,784, 9 pages.

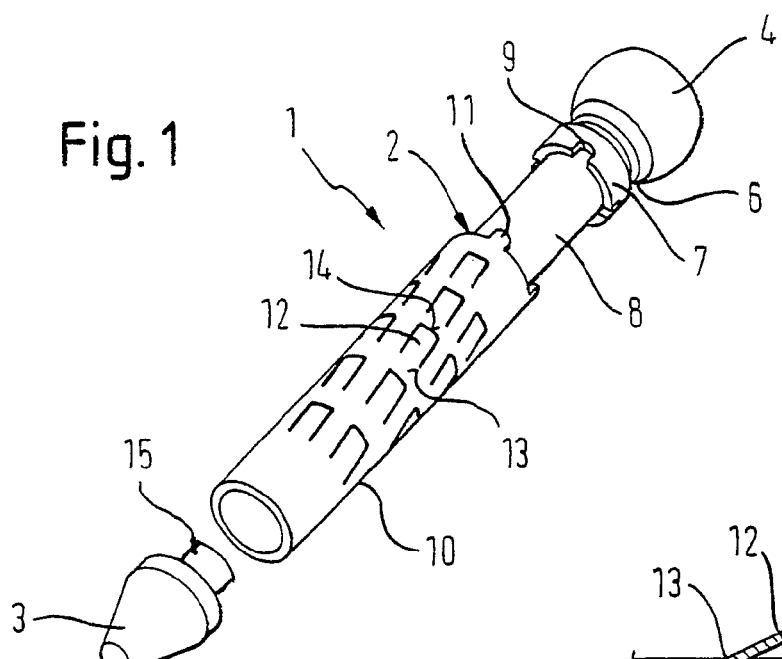
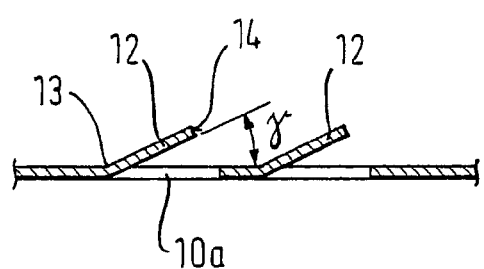
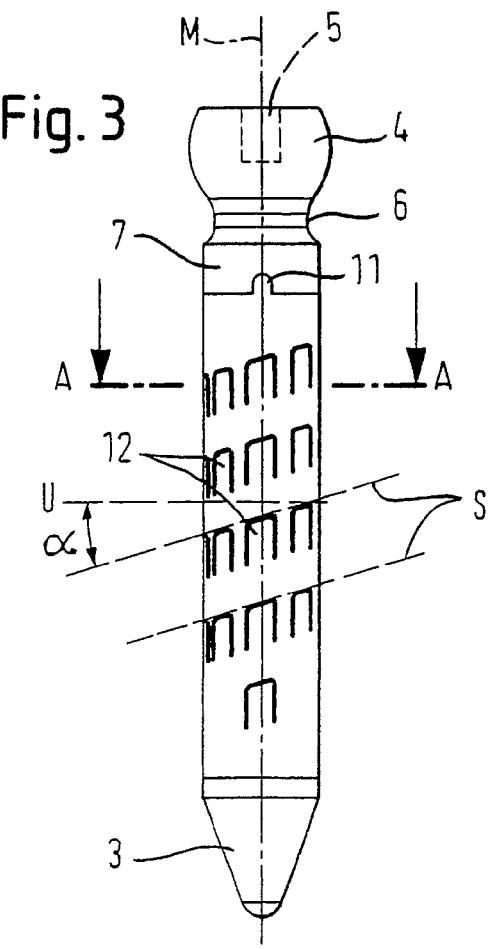
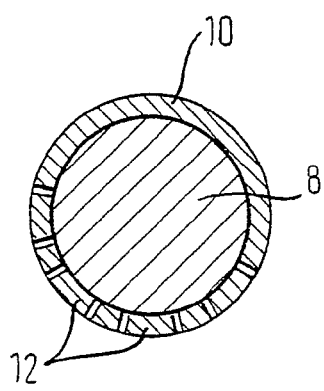

BONE ANCHORING ELEMENT

RELATED APPLICATIONS

This application is a continuation of U.S. patent application Ser. No. 11/482,374, filed Jul. 7, 2006 now U.S. Pat. No. 8,292,932 which claims the benefit of U.S. Provisional Patent Application Ser. No. 60/697,669, filed Jul. 8, 2005, and claims priority from European Patent Application EP05014839, filed Jul. 8, 2005, the entire disclosures of which are incorporated herein by reference.

BACKGROUND

The present disclosure relates to a bone anchoring element. A known form of a bone anchoring element is a bone screw having a shaft with a thread for screwing the screw into a bone. The bone screw is manually inserted into the bone by means of a screw driver, which is a time-consuming and force-requiring process. Moreover, during the process in which the screw is inserted into the bone, high pressure forces may be acting on the bone itself, which is undesirable in certain clinical applications such as e.g., in neuro surgery, spinal surgery, pediatric surgery or trauma surgery.

EP 0 714 643 A1 discloses a bone fixation device such as a screw or a pin which has a micro-textured contact surface to enhance the installation or gripping characteristics of the device. The micro-textured contact surface includes e.g. angled rasp teeth, which bite or flex to resist movement in one direction and yet flex or slide to allow a relatively easy contact movement in the other direction.

DE 198 01 219 A1 discloses a bone nail having rigid barb-like projections being arranged in circumferential rows around the nail. The barb-like projection has a saw-tooth shape which facilitates insertion of the nail as well as prevents loosening of the nail. However, a removal of the nail without destroying the bone is not possible.

CH 682450 A5 discloses an anchoring nail for the fixation of orthopedic bone implants. The nail consists of a head part and a shaft part, the shaft having retention elements provided on its outer wall which are arranged along a helical line. The retention elements are wedge-shaped and are provided with cutting edges which allow to screw out and remove the nail from the bone material. However, the core hole which has to be drilled in advance to allow an easy insertion of the nail into the bone and a removal of the nail has to have a precise diameter. In addition, the wedge-shape of the retention elements per se does not allow an easy insertion.

In view of the above, there is a need for a bone anchoring element that can remedy one or more of the above described problems associated with current bone anchoring elements.

SUMMARY

A bone anchoring element according to one or more embodiments of the present disclosure can be inserted into the bone more rapidly, more easily and with less force than conventional bone screws and nails. The bone anchoring element according to one or more embodiments of the present disclosure is versatile and useful in many clinical requirements and is easy to manufacture. The bone anchoring element according to one or more embodiments of the present disclosure does not exert damaging forces on the bone during insertion, provides for secure attachment, and then can be further inserted or can be removed in a screw-like fashion. A method for manufacturing such a bone anchoring element is also disclosed.

The bone anchoring element according to one or more embodiments of the present disclosure facilitates rapid and secure anchoring to the bone by pressing the bone anchoring element into a prepared core hole in the bone. The barb elements are arranged on at least on one helical line around the shaft axis of a tubular body part of the shaft of the bone anchoring element. The barb elements provide for a thread-like function, which allows to correct the position of the bone anchoring element in the core hole after inserting it into the core hole, by either positioning it deeper into the bone by means of a screwing-inwards motion or by screwing it backward. The barb elements prevent the bone anchoring element from being pulled out or coming loose. The bone anchoring element can be removed, if required, like a screw by turning it in the opposite or counter-clockwise direction from which it was inserted.

The bone anchoring element according to one or more embodiments of the present disclosure is easy to manufacture. If the tubular body of the shaft is made of a shape memory alloy, the shape memory effect can be used in such a way that the barb elements do not project during insertion of the bone anchoring element into the bone and rise up when the bone anchoring element is inserted due to the action of the body heat. The tubular body can also be made of a material having super elastic properties or a spring like behavior. For example a titanium alloy having super elasticity or stainless steel can be used.

Further features and advantages of the disclosed embodiments will become apparent and will be best understood by reference to the following detailed description taken in conjunction with the accompanying drawings.

BRIEF DESCRIPTION OF THE DRAWINGS

FIG. 1 shows a perspective exploded view of a bone anchoring element according to a first embodiment.

FIG. 2 shows an enlarged part of a cross-sectional view through the wall of the tubular body of the bone anchoring element of FIG. 1 in a longitudinal direction.

FIG. 3 shows a side view of the bone anchoring element according to FIG. 1 in an assembled state.

FIG. 4 shows an enlarged cross-sectional view of the bone anchoring element according to FIG. 3 along the line A-A.

DETAILED DESCRIPTION

Figure 5:
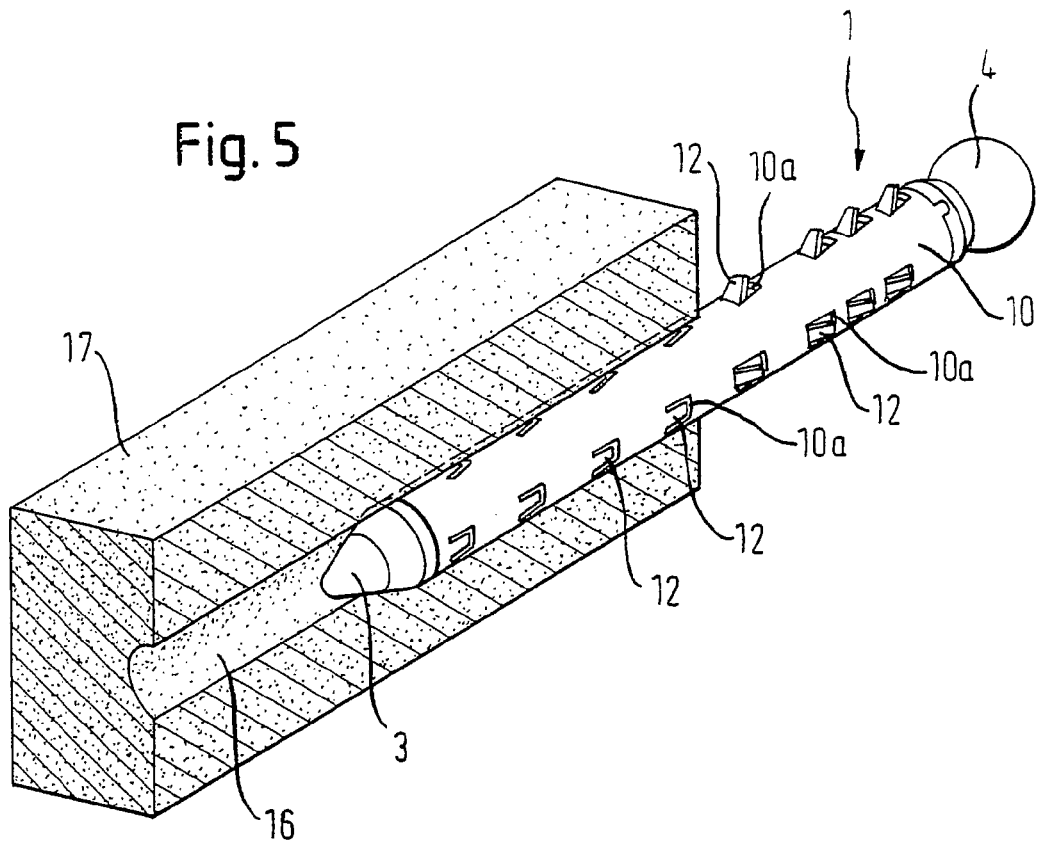
FIG. 5 shows a schematic view of a first step of the insertion of the bone anchoring element according to FIGS. 1 to 4.

A bone anchoring element 1 according to a first embodiment of the disclosure is described with reference to FIGS. 1 to 4. The bone anchoring element 1 comprises a shaft 2 with a tip 3 at one end and a head 4 at the other end. The head 4 is spherical segment-shaped and has on its free end a recess 5 for engagement with a screwing-in tool. Between the head 4 and the shaft 2 is a neck portion 6 with a circumferentially projecting shoulder 7 at the side opposite to the spherical head 4. The shoulder 7 has an outer diameter which is larger than the neck portion 6 and slightly smaller than the diameter of the head 4. Adjacent to the shoulder 7, a cylindrical first shaft part 8 is provided. The diameter of the cylindrical first shaft part 8 is smaller than the diameter of the shoulder 7. At the edge of the shoulder 7, facing the shaft part 8, a plurality of U-shaped recesses 9 are provided equidistantly in a circumferential direction which are open towards the side of the cylindrical shaft part 8.

The shaft 2 further consists of a tubular body 10 which has an inner diameter slightly larger than the outer diameter of the cylindrical shaft part 8 so that the tubular body 10 can be placed in a sliding motion onto the cylindrical shaft part 8. The outer diameter of the tubular body 10 corresponds to the outer diameter of the shoulder 7 so that when the tubular body 10 is placed onto the cylindrical shaft part 8, the outer surface of the tubular body 10 is flush with the outer surface of the shoulder 7. On its end facing the head 4, the tubular body 10 has projections 11 which correspond in their shape and arrangement to the U-shaped recesses 9 provided at the shoulder 7 for engagement when the tubular body 10 is fully placed onto the cylindrical shaft part 8. In this assembled state, the end of the tubular body 10 abuts the free end of the shoulder 7.

The tubular body 10 comprises a plurality of barb elements 12. The barb elements 12 are formed by substantially parallelogram-shaped cuts 10a being made in the wall of the tubular body 10. The end base 13 of the parallelogram-shaped cuts 10a is not cutout from the tubular body and acts as the attachment and the bending side for the barb elements 12 in the wall of the tubular body 10. The barb elements 12 are preferably arranged such that when the tubular body 10 is slid onto the cylindrical shaft part 8, the end base 13 of each barb elements 12 faces the tip 3 while the free end faces the head 4. As can be seen particularly in FIG. 3, the barb elements 12 are arranged on a helical line S around the shaft axis M. The free ends 14 of the barb elements 12 are inclined by an angle α with regard to the circular circumference line U, with the angle α corresponding to the helical angle of the helical line S. Thus, the free ends 14 of the barb element form cutting edges similar to the crest of a screw thread.

As can be seen in particular from FIG. 2, the barb elements 12 project from the surface of the tubular body 10 by an angle γ, which is selected during the manufacturing process based upon the material used and the actual dimensions of the barb elements 12 so that a desired stiffness of the barb elements 12 is obtained. Due to their configuration and attachment onto the wall of the tubular body 10, the barb elements 12 are elastically deformable relative to the tubular body 10. When the barb elements 12 are collapsed or pressed into the cuts, they are pre-tensioned.

The axial length of the tubular body 10 corresponds to the length of the cylindrical shaft part 8 so that in an assembled state a free end of the cylindrical shaft part 8 is flush with the free end of the tubular body 10. The cylindrical shaft part 8 has a cylindrical recess (not shown) at its free end to receive a correspondingly shaped cylindrical projection 15 provided at the tip 3 in a press-fit manner. The outer diameter of the base of the tip 3 corresponds to the outer diameter of the tubular body 10 so that in an assembled state, as shown in FIG. 3, the base of the tip 3 is flush with the outer wall of the tubular body 10.

The bone anchoring element 1 can be made of any body-compatible material. Preferably, a body-compatible metal, such as titanium, stainless steel and their alloys, or a body-compatible plastic material can be used. The tubular body 10 having the barb elements 12 can be made of the same material as the cylindrical shaft part 8, the head 4 and the tip 3, or of a different material if a different material is desired to ensure that the barb elements 12 have the necessary elastic properties.

Preferably, however, the tubular body 10 with the barb elements 12 can be made of a shape memory alloy having shape memory and/or super elastic characteristics, or can be made of a material having spring-like characteristics like stainless steel or titanium alloys. For example, nickel titanium alloys such as nitinol are suitable for use for the tubular body 10.

In operation, the bone anchoring element 1 is initially preassembled by sliding the tubular body 10 onto the cylindrical shaft part 8 such that the projections 11 come into engagement with the recesses 9. Thus, a rotation of the tubular body 10 on the cylindrical shaft part 8 is prevented. Thereafter, the tip 3 is firmly connected with the cylindrical shaft part 8.

Figure 6:
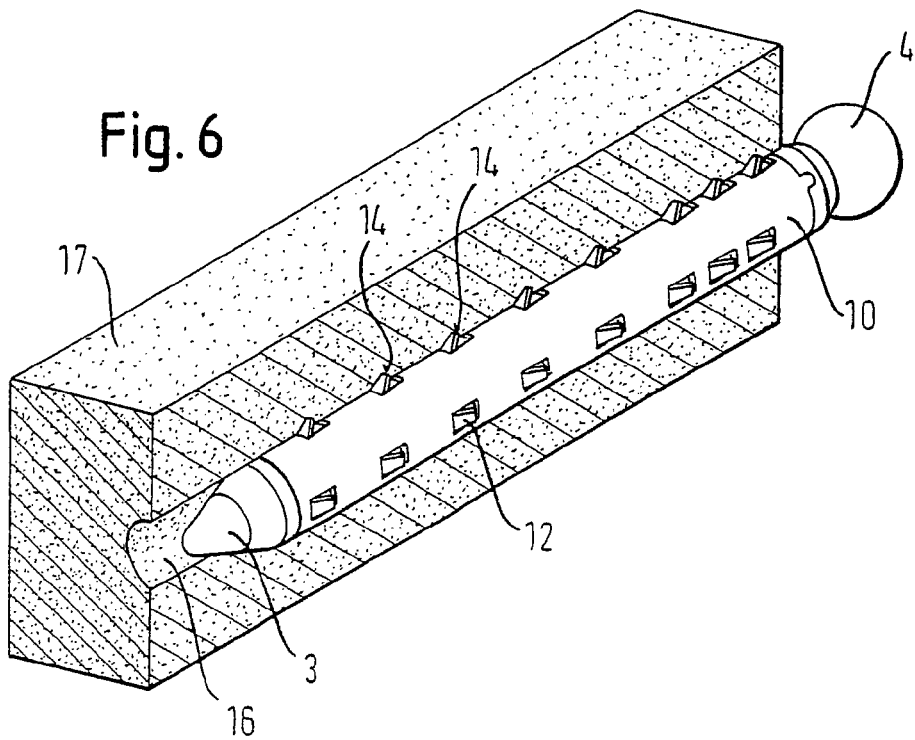
FIG. 6 shows a schematic view of the inserted state of the bone anchoring element according to FIG. 5.

In use, as is shown schematically in FIGS. 5 and 6, first a core hole 16 is prepared in the bone 17. The diameter of the core hole 16 corresponds essentially to the outer diameter of the tubular body 10 or it can be slightly larger or smaller, depending upon the desired result or circumstances. The diameter of the core hole 16 is selected depending on the diameter of the tubular body 10 and the flexibility of the barb elements 12 so that the desired resistance is provided by the barb elements 12. The selected diameter depends also upon the bone quality, for example, it can be selected larger for healthy hard bone and smaller for osteoporotic weak bone. Subsequently, as shown in FIG. 5, the bone anchoring element 1 is inserted into the core hole 16. As the bone anchoring element 1 is being inserted into the core hole 16 of the bone 17, the barb elements 12 are in a collapsed state and are pressed against or into the cuts due to their elasticity. The sliding motion enables the bone anchoring element 1 to be inserted rapidly and in a smooth way, in contrast to the conventional bone screws using the screwing-in-process. When inserted, the pre-tensioned barb elements 12 expand and rise up and press with their cutting edge 14 outwardly against the wall of the core hole 16, as is shown in FIG. 6. The barb elements 12 prevent the bone anchoring element 1 from being pulled out or from falling out of the core hole 16.

For further and/or final positioning of the bone anchoring element 1 in the core hole 16, or for positioning of the head 4, the bone anchoring element 1 is screwed further into the core hole 16 or screwed out therefrom, like a screw, by means of a turning motion with the screwing-in tool engaging the recess 5 of the head 4. During the final positioning process, the cutting edges 14 of the barb elements 12, being positioned on the helical line S, act like the crest of a thread. The bone anchoring element 1 can be removed just like a bone screw by turning it in a counter-clockwise direction.

In most cases, a conventional bone screw requires not only that the core hole 16 is drilled into the bone, but also that the bone threads are pre-cut into the bone. In all cases, with the insertion of a conventional bone screw, a repeated turning motion is required. Compared to the time required to anchor a conventional bone screw, the time required to insert the bone anchoring element 1 may be substantially shorter due to the fact that the bone anchoring element 1 slides or glides into the core hole 16 without having to encounter the forces of the screw thread on the core hole 16 and the bone 17. Nonetheless, because of its design and configuration, the bone anchoring element 1 does not fall out of the core hole 16. Also, when a conventional bone screw is inserted, it cuts with the thread crest in the bone material.

A process for manufacturing the bone anchoring element 1 may include providing a cylinder having a diameter corresponding to that of the tubular body 10, the cylinder being made of a material which is desired for the tubular body 10, preferably a shape memory alloy or another metallic material or an alloy with flexible properties. In a next step, a coaxial bore is provided in the cylinder such that a tubular body 10 is prepared. Thereafter, the barb elements 12 are generated by means of cutting, for example laser cutting, parallelogram-shaped cuts in the wall of the tubular body 10 in which one side which shall be the base of the barb elements 12 is not cut out. Thereafter the barb elements 12 are bent such that they project to the outside.

Modifications of the first embodiment are possible. The head 4 needs not to be spherical segment-shaped but can have another shape, in particular it can have any shape of known screw heads. The recesses 9 and the corresponding projections 11 need not to be U-shaped but can have a different shape. At least one recess 9 and a corresponding projection 11 is necessary to provide securing against rotation. However, it is also possible to prevent rotation by different means. For example, a pin (not shown) which can be inserted into a transverse bore (not shown) provided in the tubular body 10 and the cylindrical shaft part 8 can be used.

The barb elements 12 need not have only a parallelogram-shape, but can have another shape, as long as the cutting edges 14 lie on at least one helical line. For example, the barb elements 12 can have a trapezoidal shape. The pitch of the helical line may vary along the length of the tubular body 10. The barb elements 12 need not to be provided over the whole length of the tubular body 10 but can be provided also only in a section of the tubular body 10. The distance between the barb elements 12 may also vary.

In yet another embodiment of the disclosure, if the tubular body 10 including the barb elements 12 is made from a shape memory alloy, the tubular body 10 is treated before assembly of the bone anchoring element 1 in such a way so that the barb elements 12 project at a body temperature or at an elevated temperature and are in a collapsed position at a lower temperature, e.g. at room temperature. In operation, the bone anchoring element 1 with collapsed barb elements 12 is pressed into the core hole 16. After the bone anchoring element 1 warms up and equilibrates to the body temperature or is heated through an external device, the barb elements 12 expand to their final position. This provides the advantage that it reduces the amount of force that is required to press the bone anchoring element 1 into the core hole 16 and enables the adjustment of the bone anchoring element 1 to a desired depth by the sliding motion during its insertion as long as the barb elements 12 are in a collapsed state and do not press against the wall of the core hole 16. If the tubular body 10 has super elasticity in addition to shape memory characteristics, the higher elasticity of the barb elements 12 simplifies the handling and provides additional security in anchoring the bone anchoring element 1 in the bone.

Figure 7:
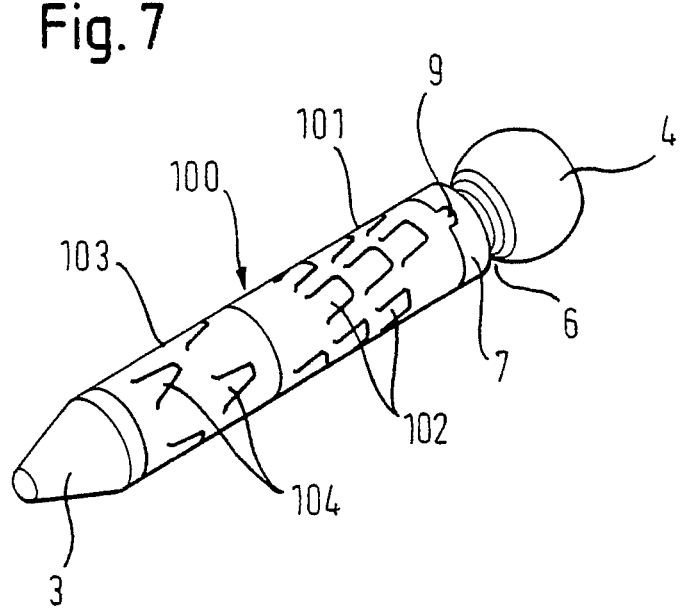
FIG. 7 shows a perspective view of a second embodiment of the bone anchoring element.

In the second embodiment shown in FIG. 7, those parts which correspond to the parts of the first embodiment are characterized with the same reference numerals. The bone anchoring element 1 of the second embodiment differs from the bone anchoring element according to the first embodiment in that the tubular body 100 comprises two sections. A first section 101 with barb elements 102 having a first distance from each other in a circumferential direction and having substantially parallelogram-shape, and a second section 103 having barb elements 104 which have a second distance from each other in the circumferential direction which is larger than the first distance of the barb elements 102 in the first section 101. Hence, the barb elements 104 in section 103 are less densely arranged than the barb elements 102 in section 101. The barb elements 104 are substantially V-shaped. The bone anchoring element 1 is particularly suitable for application in the spinal column, in particular for anchoring in the vertebra. The second section 103 with the larger distance between the barb elements 104 is provided adjacent to the tip 3 and comes into engagement with the vertebral body. The first section 101 is adjacent to the head and comes into engagement with the pedicle. Thus, due to the larger distance between the barb elements 104 in the vertebral body, any potential damage of the vertebral body can be minimized while providing higher locking forces of the barbs 102 in the pedicle area.

In the embodiment shown in FIG. 7, the tubular body 100 is made of one single tube. However, the tubular body 100 with sections 101, 103 having different characteristics of the barb elements 102, 104, respectively, can be made of two separate tubular bodies. In such a case, it is necessary to prevent rotation between the two tubular bodies. This can be realized, for example, by providing recesses (not shown) at the end of the first tubular body in which projections of the second tubular body engage.

Modifications are possible, for example, more than two sections with different characteristics of the barb elements can be provided.

Figure 8:
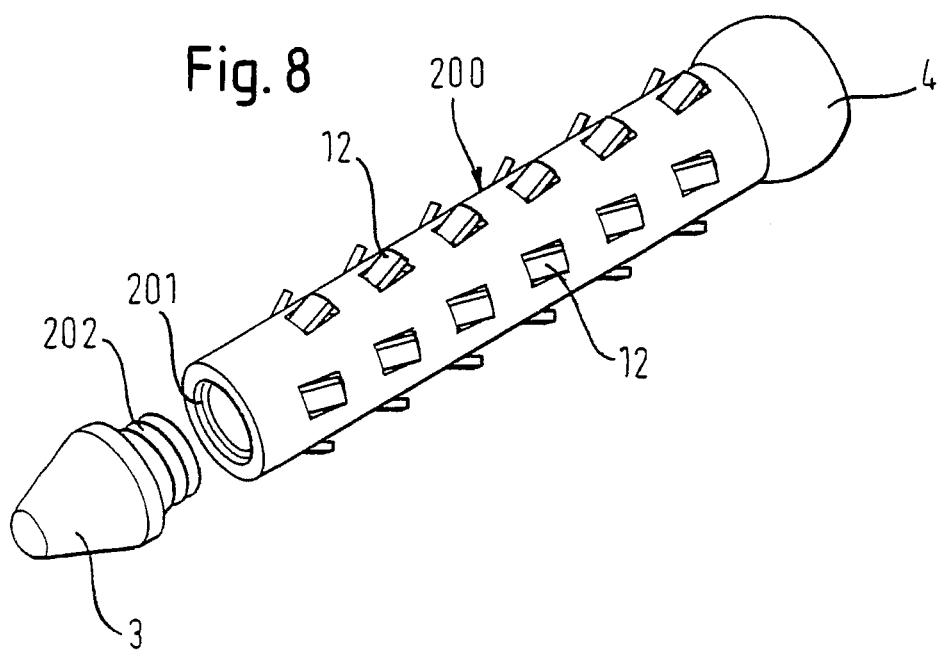
FIG. 8 shows a third embodiment of the bone anchoring element.

FIG. 8 shows a third embodiment of the disclosure. The shaft of the bone anchoring element 1 is not composed of the cylindrical shaft part 8 and the tubular body 10, but includes a tubular body 200 only. Thus, the shaft is hollow. At its end facing the tip 3, the tubular body 200 comprises a section with an inner thread 201 which cooperates with an outer thread 202 on the cylindrical projection of the tip 3. Alternatively, the tip 3 can also be connected in a press-fit manner to the tubular body 200. The tubular body 200 comprises the barb elements 12 as in the previous embodiments. Different sections with different shapes and/or distances of barb elements 12 can be provided as in the embodiment shown in FIG. 7. Also, the pitch of the helical line S can vary along the length of the tubular body 200. The head 4 is either formed integrally with the tubular body 200 or comprises a projection with an outer thread which can be screwed into the other end of the tubular body 200 which has a corresponding inner thread. Alternatively, the head 4 can be connected in a press-fit manner to the tubular body 200. The bone anchoring element according to the third embodiment is particularly simple to manufacture.

Figure 9:
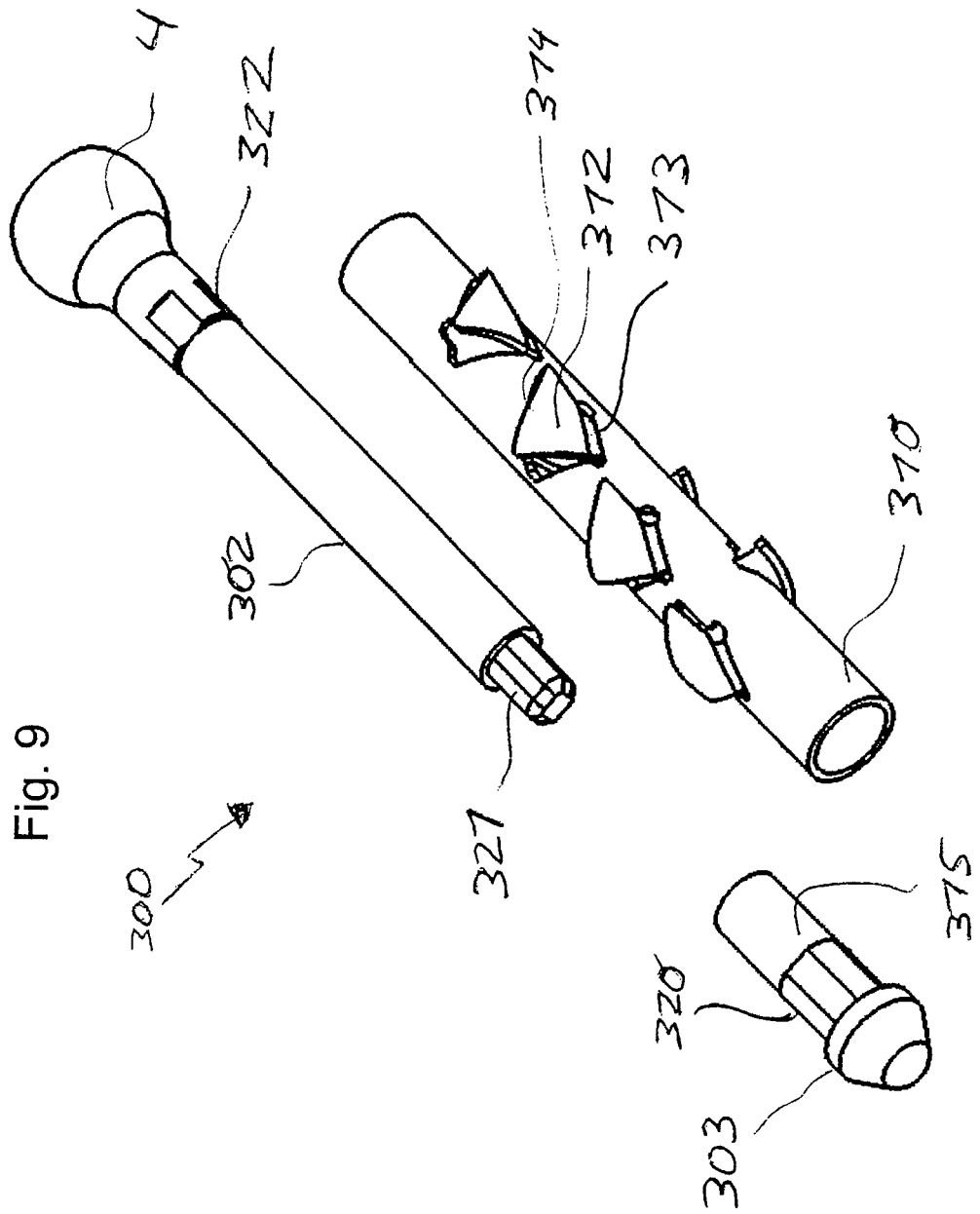
FIG. 9 shows an exploded view of a fourth embodiment of the bone anchoring element.

FIG. 9 shows an exploded view of a fourth embodiment of the disclosure. The bone anchoring element 300 according to FIG. 9 comprises a tip 303, a tubular body 310 and a shaft 302 provided with a head 4 at one end. The fourth embodiment differs from the above described first embodiment in that barb elements 312 are provided instead of the barb elements 12 of the first embodiment. Further, the fourth embodiment differs from the first embodiment in the structures for connecting the tip 303, the shaft 302 and the tubular body 310.

First, the barb elements 312 will be described with reference to FIG. 9. As can be seen in FIG. 9, in top view the barb elements 312 have the contour of an irregular quadrangle which is twisted so that it has a curvature. The free ends 314 of the barb elements 312 lie substantially on a helical line. The width of the free ends 314 of the barb elements 312 is larger than the width of the end base 313 of the barb elements 312. As a result, the width of the free ends 314 is enlarged as compared to first embodiment which provides a stable construction and an enlarged contact surface of the free ends 314 with the bone into which the bone anchoring element is to be inserted. The free ends 314 of the barb elements form a helical line around the axis of the shaft 302 with the pitch of the helical line enlarged as compared to the first embodiment.

The large pitch of the helical line allows fast adjustment of the position of the bone anchoring element in the bone by further screwing-in into the bone or unscrewing from the bone, respectively.

As can be seen in FIG. 9, a first connecting structure 320 is provided on the projection 315 of tip 303. This first connecting structure 320 serves to cooperate with the inner bore of the tubular body 310 for establishing a fixation between the tip 303 and the tubular body 310. Further, a second connecting structure 321 is provided on the shaft 302 on the side directed towards the tip 303. This second connecting structure 321 cooperates with a corresponding connecting structure (not shown) provided in a concentric inner bore which is provided in the projection 315 of the tip 303 on the side directed towards the shaft 302 and serves to establish a fixation between the tip 303 and the shaft 302. Furthermore, a third connecting structure 322 is provided on the outer circumference of the shaft 302 on the side of the head 4. This third connecting structure 322 cooperates with the inner bore of the tubular body 310 on the side directed towards the head 4 in order to establish a fixation between the shaft 302 and the tubular body 310 on the side of the head 4.

In the embodiment shown, the first connecting structure 320 is provided by forming a part of the projection 315 with a substantially square cross-section with rounded edges. When fitted into the inner bore of the tubular body 320, this shape leads to a distortion-fit connection. The second connecting structure 321 is provided by forming an end of the shaft 302 with a substantially square cross-section with rounded edges. The corresponding connecting structure in the inner bore of the projection 315 is formed by a recess with a substantially square cross-section with rounded edges into which the second connecting structure 321 can be fitted such that positive locking as well as press-fit is achieved. Similar to the first connecting structure 320, the third connecting structure 322 is provided by forming a part of the shaft 302 on the side of the head 4 with a substantially square outer cross-section with rounded edges so that a distortion-fit connection to the tubular body can be achieved.

In the embodiment, the fixation of the tip 303 and the tubular body 310 is achieved by distortion locking, the fixation of the tubular body 310 and the shaft 302 on the side of the head 4 is achieved by distortion locking, and the fixation of the tip 303 and the shaft 302 is achieved by positive locking and frictional locking.

By providing the first connecting structure 320, the second connecting structure 321 and the third connecting structure 322 three sections for transmitting torsional forces are provided in the fourth embodiment. This results in improved properties during insertion into the bone and removal from the bone.

The shape of the first, the second and the third connecting structures is not limited to a square shape with rounded edges. For example, hexagonal shapes, octagonal shapes etc. with or without rounded edges are possible as well.

In all embodiments described above the diameter of the tubular body can vary over the axial length of the tubular body, for example it can decrease towards the tip so that the tubular body has a conical outer surface.

The bone anchoring element 1 can be used together with a plate to establish a bone fixing device or with a receiver part to be connected with a rod to establish a spinal fixation system. Also, all further applications are conceivable in which the bone anchoring element 1 can be used instead of conventional bone screws or instead of conventional pins used in a bone anchoring manner.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring element having a shaft for anchoring in a bone, the shaft comprising:
    a plurality of barb elements;
    a tubular body defined by a peripheral wall, the peripheral wall defining an interior space of the tubular body extending along a shaft axis from a first end to a second end of the tubular body;
    an inner body comprising a shaft part and a head, the shaft part configured to be located in the interior space of the tubular body;
    wherein each barb element comprises a base formed in one piece with the tubular body, opposing side edges extending from the base, and a free cutting edge opposite to the base and extending between the side edges;
    wherein each of the plurality of barb elements is movable from a collapsed position adjacent to a surface of the tubular body to an expanded position farther from the surface of the tubular body than the collapsed position to define an opening completely through the peripheral wall to the interior space of the tubular body; and
    wherein the tubular body and the inner body have corresponding engagement elements that prevent rotation of the tubular body relative to the inner body when the inner body is located in the interior space of the tubular body, the head is located outside of the interior space of the tubular body, and the engagement elements are engaged.

2. A bone anchoring element having a shaft for anchoring in a bone, the shaft comprising:
    a plurality of barb elements;
    a tubular body;
    wherein each barb element comprises a base formed in one piece with the tubular body, opposing side edges extending from the base, and a free cutting edge opposite to the base and extending between the side edges;
    wherein each of the plurality of barb elements is movable from a collapsed position adjacent to a surface of the tubular body to an expanded position farther from the surface of the tubular body than the collapsed position;
    wherein each of the barb elements has a curvature corresponding to a curvature of the shaft; and
    wherein a distance between the side edges is greater than a width of the base.

3. The bone anchoring of claim 2, wherein the tubular body is defined by a peripheral wall and said barb elements are cut out of the peripheral wall of said tubular body.

4. The bone anchoring element of claim 2, wherein the tubular body is defined by a peripheral wall, the peripheral wall defining an interior space of the tubular body extending along a shaft axis from a first end to a second end of the tubular body.

5. The bone anchoring element of claim 4, wherein the expanded position of each of the plurality of barb elements defines an opening completely through the peripheral wall to the interior space of the tubular body.

6. The bone anchoring element of claim 2, wherein said tubular body is placed onto an essentially cylindrical shaft.

7. The bone anchoring element of claim 6, wherein the tubular body is coupled to the shaft to prevent rotation of the tubular body relative to the shaft.

8. The bone anchoring element of claim 6 further comprising a head connectable to the tubular body, wherein fixation of the tubular body and the shaft on the side of the head is achieved by distortion locking.

9. The bone anchoring element of claim 6, further comprising a tip connectable to the tubular body, wherein fixation of the tip and the shaft is achieved by positive locking and frictional locking.

10. The bone anchoring element of claim 2, further comprising a tip fixedly connectable to said tubular body.

11. The bone anchoring element of claim 10, wherein the tip is fixedly connectable to said tubular body by one of a press-fit or a threaded connection.

12. The bone anchoring element of claim 2, further comprising a head connectable to said tubular body.

13. The bone anchoring element of claim 2, wherein said tubular body is formed of a shape memory alloy.

14. The bone anchoring element of claim 13, wherein the shape memory alloy is nitinol.

15. The bone anchoring element of claim 2, further comprising a tip connectable to the tubular body by distortion locking.

* * * * *